United States Patent [19]

Taheri

[11] Patent Number: 4,586,919
[45] Date of Patent: May 6, 1986

[54] EXTERNAL SHUNT AND METHOD FOR PROCURING AND PRESERVING THE ENDOTHELIUM OF A VEIN USED IN ARTERIAL BYPASS

[76] Inventor: Syde A. Taheri, 268 Dan Troy, Williamsville, N.Y. 14221

[21] Appl. No.: 597,706

[22] Filed: Apr. 6, 1984

[51] Int. Cl.$^4$ .............................................. A61M 5/00
[52] U.S. Cl. ........................................ 604/9; 604/32; 604/179
[58] Field of Search .......................... 604/9, 7, 8, 4, 32, 604/280, 283, 284, 179, 52, 53; 188/DIG. 26

[56] References Cited

U.S. PATENT DOCUMENTS

| | | | |
|---|---|---|---|
| 1,850,132 | 3/1932 | Morse | 604/7 |
| 2,935,068 | 5/1960 | Donaldson | 604/8 X |
| 3,851,646 | 12/1974 | Sarns | 604/284 X |
| 3,859,985 | 1/1975 | Eckhart | 604/9 |
| 3,882,862 | 5/1975 | Berend | 604/8 |

Primary Examiner—Stephen C. Pellegrino
Attorney, Agent, or Firm—Joseph P. Gastel

[57] ABSTRACT

A shunt for attachment between an artery and a vein being harvested for use in an arterial bypass including an elongated tube, a first end on the elongated tube for insertion into a femoral artery, a second end on the elongated tube for insertion into the distal portion of a saphenous vein to thereby maintain communication between the artery and the vein even though normal blood flow to the vein is disrupted, a stopcock between the first and second ends, a second elongated tube coupled to the stopcock for selectively receiving blood from the elongated tube to irrigate the external portion of the vein being harvested, and a detachable connection at the second end of the elongated tube for selectively permitting detachment of the second end of the elongated tube from the remainder of the elongated tube during vein harvesting. A method of harvesting a section of vein for use in a remote portion of a person's body to effect an arterial bypass about a diseased portion of an artery having a diseased proximal portion and a diseased distal portion including the steps of harvesting a section of vein having a distal portion and a proximal portion, maintaining blood flow through the vein from its distal portion toward its proximal portion during the harvesting, effecting a first anastamosis between the proximal portion of the vein section and the artery distal to its diseased distal portion, and effecting a second anastamosis between the distal portion of the vein section and the artery proximal to its diseased proximal portion, to thereby effect the arterial bypass.

10 Claims, 4 Drawing Figures

U.S. Patent      May 6, 1986      4,586,919
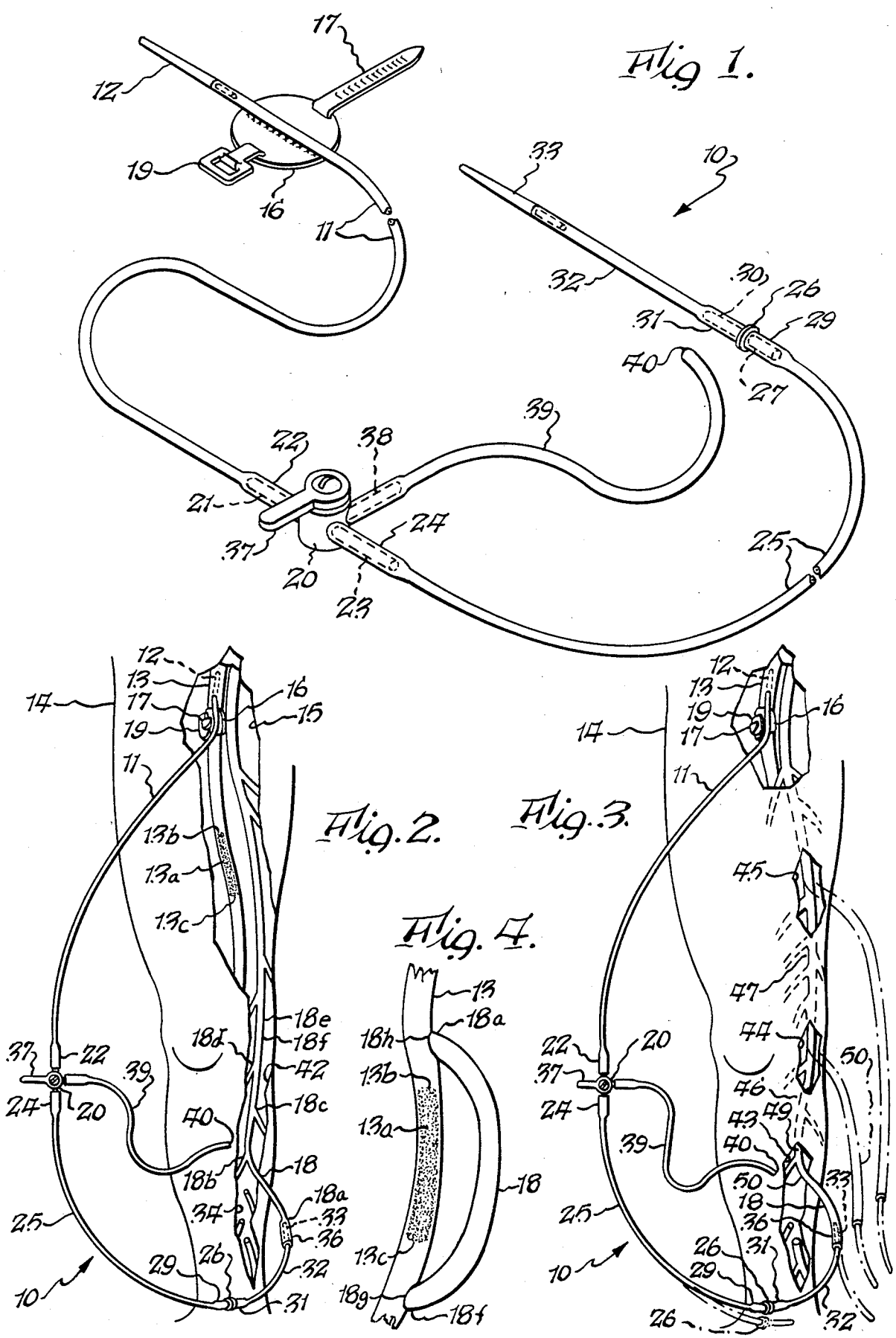

EXTERNAL SHUNT AND METHOD FOR PROCURING AND PRESERVING THE ENDOTHELIUM OF A VEIN USED IN ARTERIAL BYPASS

BACKGROUND OF THE INVENTION

The present invention relates to an external shunt and method for procuring and preserving the endothelium of a vein which is being harvested for use as an arterial bypass.

By way of background, it has been found that it is difficult to maintain patency of veins being harvested for arterial bypasses. It is believed that this lack of patency results in the deterioration of the venous endothelium which is deprived of blood during the harvesting process. It is further believed that the failure to preserve the venous endothelium may result in intimal damage resulting in thrombosis, stenosis and accelerated atherosclerosis. It is with overcoming the foregoing deficiencies that the present invention is concerned.

SUMMARY OF THE INVENTION

It is one object of the present invention to provide an external shunt for providing arterial blood to a vein during harvesting of the latter for arterial bypass, to therey preserve the venous endothelium and thus prevent subsequent thrombosis, stenosis and accelerated atherosclerosis after the arterial bypass has been effected.

The present invention also relates to an improved method for harvesting a vein for arterial bypass. Other objects and attendant advantages of the present invention will readily be perceived hereafter.

The present invention relates to a shunt from an artery to a vein being harvested for use in a remote portion of a body comprising an elongated tube, a first end on said elongated tube for insertion into an artery, a second end on said elongated tube for insertion into a distal portion of a vein to thereby maintain communication between said artery and said vein even though normal blood flow thereto is disrupted, valve means intermediate said first and second ends, and a second elongated conduit coupled to said valve means for selectively receiving blood from said first conduit to irrigate the external portion of said vein being harvested.

The present invention also relates to a method of harvesting a section of vein for use in a remote portion of a person's body to effect an arterial bypass about a diseased portion of an artery having a diseased proximal portion and a diseased distal portion comprising the steps of harvesting a section of vein having a distal portion and a proximal portion, maintaining blood flow through said vein from its distal portion toward its proximal portion during said harvesting, effecting a first anastamosis between said proximal portion of said vein section and said artery distal to said diseased distal portion of said artery, and effecting a second anastamosis between said distal portion of said vein section and said artery proximal to said diseased proximal portion of said artery, to thereby effect said arterial bypass.

The various aspects of the present invention will be more fully understood when the following portions of the specification are read in conjunction with the accompanying drawings wherein:

BRIEF DESCRIPTION OF THE DRAWINGS

FIG. 1 is a fragmentary perspective view of the external shunt of the present invention;

FIG. 2 is a fragmentary perspective view of a person's leg with the shunt in place at the beginning of a vein harvesting operation;

FIG. 3 is a fragmentary perspective view similar to FIG. 2 but showing progressive steps during another type of vein harvesting operation; and FIG. 4 is a fragmentary enlarged view of a portion of FIG. 3 showing the details of a completed arterial bypass.

DESCRIPTION OF THE PREFERRED EMBODIMENTS

Summarizing briefly in advance, the external shunt and method of the present invention are primarily for the purpose of procuring a section of vein and preserving its endothelium, said section of vein being subsequently used for an arterial bypass. This is done by essentially maintaining a blood flow under pressure to the vein being harvested to thereby maintain its patency.

The external shunt 10 includes an elongated tube consisting of a first tube portion 11 and a second tube portion 25. Tube 11 is mounted on a tubular end member 12 which is inserted into the common femoral artery 13 of the person's leg 14 after the patient has been put under an general or spinal anesthesia and after a routine preparation and drape have been effected and after a longitudinal incision 15 has been made in the groin and after the common femoral, superficial femoral, and profunda arteries have been identified and isolated. A tab 16 is permanently secured to tube 11 proximate end 12 and has a strap 17 extending from one side of tab 16 and a buckle 19 extending from the other side of tab 16. End member 12, which is preferably tapered for easy insertion into an incison in the femoral artery, is maintained in its inserted position by placing tab 16 against the artery and securing strap 17 into buckle 19 after strap 17 has been wound around the rear of the artery, as shown in FIG. 2. After this has been done, end member 12 is maintained securely in position.

A stopcock 20 has a entry conduit 21 on which the end 22 of tube 11 is mounted. Another conduit 23 is associated with stopcock 20 and mounts the end 24 of tube 25. A connector or coupling member 26 in the nature of a nipple has a conduit 27 which mounts the end 29 of conduit 25. Connector member 26 also has a conduit 30 which mounts the end 31 of conduit 32 which in turn mounts a tapered tubular end member 33 at its outer end. Connector 26 is used only in one particular type of surgical procedure, as described hereafter. Thus, if this particular procedure is not used, connector 26 may be omitted, and tubular portions 25 and 32 may be integral.

After the end member 12 has been inserted into the femoral artery, as described above, a parallel incision is made over the medial aspect of the malleolus in the area 34 of the patient's leg to isolate and control the distal portion of saphenous vein 18. A suitable amount of heparin is injected into the patient, this amount being approximately 5,000 units.

As noted above, the proximal end member 12 has been inserted into an incision into the femoral artery. The distal portion of the saphenous vein is tied off, and the portion of the saphenous vein proximal to the tied off portion is severed. The distal portion of the shunt, namely, the end member 33 is inserted into the severed end of the saphenous vein at 18a and secured with a suture at 36. When the handle 37 of stopcock 20 is moved to cause the valve therein to move from a closed to an open position, blood will flow from the common femoral artery 13 through conduit 11, stopcock 20, conduit 25, and conduit 32 into the severed end of the distal saphenous vein to thus maintain patency and circulation.

After the foregoing blood flow through the shunt from end member 12 to end member 33 has been established, the saphenous vein 13 is harvested with gentle dissection. The initial blood flow into the saphenous vein is measured by suitable instrumentation well known in the art, and pressure is obtained to maintain the vein under pressure and against collapse. The pressure of blood flow to the saphenous vein can be adjusted by varying the opening through the stopcock by manipulating the position of stopcock handle 37 which adjusts the opening of the valve therein. As division of the collateral vessels ensue and as they are tied off at points such as 18b, 18c and 18d, etc., the flow to the proximal vein will increase, as will the pressure thereto. As noted above, the pressure may be adjusted by varying the opening through the valve in stopcock 20.

The proper length of vein is harvested and the length of the required vein is predetermined with a silk suture at point 18e, for example. After the proper length of vein is obtained by dissection, the vein is divided or cut off at point 18f proximal to severed end 18a but distal to the suture at 18e to provide a length or section of vein having an open end at 18f. A biopsy specimen taken from a segment of the harvested vein may be used for scanning and light electron microscopy. The vein is then reversed, and a tunnel is created leading to the diseased portion 13a of the artery having a diseased proximal portion 13b and a diseased distal portion 13c. A first anastamosis is made at 18g between the cut off open end 18f of vein 18 of the saphenous vein and the artery 13 distal to diseased portion 13c. As noted above, patency of the vein is obtained by maintaining flow of arterial blood through vein 18 while the end members 12 and 33 of the shunt are in place. Thereafter, a second anastamosis is made at 18h proximal to diseased proximal portion 13b of the artery 13 (FIG. 4) between the distal open end 18a of the section of the saphenous vein and the artery 13 proximal to diseased proximal portion 13b of the artery 13.

During the process of dissecting the vein, stopcock 20 is normally maintained in an open condition to maintain blood pressure in the saphenous vein. This maintains the vein extended and also provides the necessary blood flow to preserve the endothelium.

The stopcock 20 includes a side arm conduit 38 which mounts a tube 39 having an open end 40. The valve within stopcock 20 is periodically moved by handle 37 to establish communication between conduit 11 and conduit 39 to permit arterial blood to flow out of end 40. This blood flow is used to periodically irrigate the portions of the saphenous vein which are being harvested and which are exposed, to thereby prevent dryness. As noted above, blood flow is maintained in the saphenous vein throughout the harvesting procedure with arterially oxygenated blood at systemic pressure, thereby preserving the venous endothelium for future use in arterial bypass procedures.

The above described external shunt used in saphenous vein harvesting minimizes trauma to the section of vein being removed for the arterial bypass. By preserving intimal integrity, late graft failure after arterial bypass is believed to be lessened, such failure being due to intimal damage resulting in thrombosis, stenosis and accelerated atherosclerosis. The above described external shunt and method enhances the ease of vein harvesting by keeping the vein distended so that all branches may be accurately identified, and further the procedure maintains vein moistness. During the harvesting, the above-described external shunt and method is instrumental in maintaining a constant vein distending pressure and temperature, thus preventing physiologic variation which may damage the endothelium. Scanning and light electron microscopy have indicated that endothelial integrity has been maintained by the use of the above-described external shunt construction and method of harvesting.

In FIG. 3 an alternate method of removing the distal portion of the saphenous vein is portrayed. This method is identical to that described in detail above and uses the exact external shunt 10 described above. However, in this procedure instead of having a continuous incision 42, such as shown in FIG. 2, a plurality of spaced incisions 43, 44 and 45 are made while integrity of the leg is maintained at intermediate portions 46 and 47 to lessen the amount of external incision. After the end member 33 has been attached to the vein 18 at 36, a length of vein is dissected to point 49. Thereafter, a tunnel is made through the portion of the leg 46. Tube 32 is then separated from conduit 30 of connector 26, and the end portion 50 of the vein with tube 32 attached thereto is pulled through the tunnel at 46 and pulled out of the leg as indicated in dotted lines at the lower right-hand portion of FIG. 3. Thereafter, the end 31 of tube 32 is remounted on conduit 30 of connector 26. Thus, every time the vein has to be pulled through a tunnel which is made in leg portion 46 between incisions 43 and 44 and in leg portion 47 between incisions 44 and 45, end 31 of tube 32 is disconnected from connector conduit 30, and after the vein has been pulled out of the leg as shown in FIG. 3, conduit end 31 is remounted on connector conduit 30. The valve within stopcock 20 is closed whenever tube end 31 is disconnected from connector conduit 30 to thus prevent loss of blood from artery 13.

It will be appreciated that the use of connector 26 is solely for the purpose of harvesting veins by the method described above relative to FIG. 3. However, if this method is not to be used, connector 26 may be omitted in its entirety from the external shunt 10 of FIG. 1, in which event the end member 33 would be mounted at the end of conduit 25.

End members 12 and 33 are tapered for easy insertion into the incised artery and vein, respectively, and that the tubes 11, 25 and 32 are preferably of four millimeter internal diameter. The tubes may be made of suitable plastic material which is sufficiently flexible for ease of handling and which can be maintained packaged in a sterile condition for use. The stopcock 20 is the type which has a valve therein which will prevent flow from stopcock conduit 21 to both stopcock conduits 23 and 37, or it may permit communication between stopcock conduit 21 and stopcock conduit 23 or stopcock conduit 37, but not both simultaneously.

While the foregoing portion of the specification has described the arterial bypass with respect to a diseased portion of a femoral artery, it will be appreciated that the procedure is applicable to any type of arterial bypass including that of the coronary artery. Furthermore, while the preceding portion of the specification has referred to a diseased portion of an artery, this is meant to include blockage and any other trauma which can be treated by a bypass procedure.

While preferred embodiments of the present invention have been disclosed, it will be appreciated that it is not limited thereto, but may be otherwise embodied within the scope of the following claims.

What is claimed is:

1. A shunt from an artery to a vein being harvested for use in a remote portion of a body comprising a first elongated tube, a first end on said first elongated tube for insertion into an artery, a second end on said first elongated tube for insertion into a distal portion of a vein to thereby maintain communication between said artery and said vein even though normal blood flow thereto is disrupted, valve means intermediate said first and second ends of said first elongated tube, a second elongated tube having first and second ends, said first end of said second elongated tube being coupled to said valve means for selectively receiving blood from said first elongated tube when said valve means are open, said second end of said second elongated tube being open to direct blood flowing through said second elongated tube to irrigate the external portion of said vein being harvested, securing means for securing said first end of said elongated tube to said artery, said securing means comprising a planar tab secured to said elongated tube proximate said first end, and strap means mounted on said planar tab.

2. A shunt from an artery to a vein being harvested for use in a remote portion of a body comprising a first elongated tube, a first end on said first elongated tube for insertion into an artery, a second end on said first elongated tube for insertion into a distal portion of a vein to thereby maintain communication between said artery and said vein even though normal blood flow thereto is disrupted, valve means intermediate said first and second ends of said first elongated tube, a second elongated tube having first and second ends, said first end of said second elongated tube being coupled to said valve means for selectively receiving blood from said first elongated tube when said valve means are open, said second end of said second elongated tube being open to direct blood flowing through said second elongated tube to irrigate the external portion of said vein being harvested, and securing means for securing said first end of said elongated tube to said artery, said securing means comprising strap means secured to said elongated tube proximate said first end.

3. A method of harvesting a vein for an arterial bypass and effecting said arterial bypass about a diseased portion of an artery having a diseased proximal portion and a diseased distal portion comprising the steps of severing a distal end of a vein to provide a first open end, connecting said first open end of said vein to an artery by means of a tube to maintain blood flow to said vein from said artery, harvesting said vein from said first open end toward the proximal portion thereof, cutting off a section of said vein extending proximally from said first open end to provide a second open end remote from said first open end, effecting a first anastamosis between said second open end and said diseased artery distally to said diseased distal portion of said artery, and effecting a second anastamosis between said first open end and said diseased artery proximal to said diseased proximal portion of said artery, to thereby cause said section of said vein to constitute a bypass about said diseased portion of said artery.

4. A method of harvesting a vein as set forth in claim 3 including the step of irrigating the external portion of said vein which is being removed with blood from said person.

5. A method of harvesting a vein as set forth in claim 4 wherein said blood used for irrigating is obtained from said artery.

6. A method of harvesting a vein as set forth in claim 3 wherein said artery is the common femoral artery and wherein said vein is the saphenous vein.

7. A method of harvesting a vein as set forth in claim 3 wherein said artery to which said distal portion of said vein is connected is the femoral artery and wherein said vein is the saphenous vein, and wherein said diseased artery is an artery other than said femoral artery.

8. A method of harvesting a vein for use in another portion of a person's body to bypass a diseased portion of an artery having a diseased proximal portion and a diseased distal portion comprising the steps of making a first incision in the body and isolating a predetermined artery, making a second incision in the body and isolating a distal portion of a vein having a distal portion and a proximal portion, inserting a first end of a tube into said predetermined artery, tying off said distal portion of said vein, severing said vein proximal to said portion which has been tied off to provide a first open end in communication with said proximal portion of said vein, inserting a second end of said tube into said open end of said vein to maintain blood flow thereto from said artery, harvesting said vein from said distal portion toward said proximal portion while blood flow thereto is maintained, tying off a proximal portion of said vein being harvested, cutting off a desired length of said vein distal to said tied off proximal portion to provide a section of said vein having a second open end remote from said first open end, effecting a first anastomosis between said second open end of said vein and said artery distal to said diseased distal portion of said artery, removing said second end of said tube from said said first open end of said vein, and effecting a second anastamosis between said first open end of said vein and said artery proximal to said diseased proximal portion, to thereby cause said segment of said vein to function as a bypass about said diseased portion of said artery.

9. A method of harvesting a section of vein for use in a remote portion of a person's body to effect an arterial bypass about a diseased portion of an artery having a diseased proximal portion and a diseased distal portion comprising the steps of harvesting a section of vein having a distal portion and a proximal portion, maintaining blood flow through said vein from its distal portion toward its proximal portion during said harvesting, effecting a first anastamosis between said proximal portion of said vein section and said artery distal to said diseased distal portion of said artery, and effecting a second anastomosis between said distal portion of said vein section and said artery proximal to said diseased proximal portion of said artery, to thereby effect said arterial bypass.

10. A method as set forth in claim 9 wherein said blood flow through said section is maintained until after said first anastamosis has been made.

* * * * *